United States Patent [19]

Matsumura et al.

[11] Patent Number: 4,464,530

[45] Date of Patent: Aug. 7, 1984

[54] PROCESS FOR PRODUCTION OF SUGAR KETALS

[75] Inventors: Koichi Matsumura, Ibaraki; Tetsuya Aono, Nagaokakyo, both of Japan

[73] Assignee: Takeda Chemical Industries, Ltd., Osaka, Japan

[21] Appl. No.: 478,201

[22] Filed: Mar. 23, 1983

[30] Foreign Application Priority Data

Mar. 29, 1982 [JP] Japan .................................. 57-50574

[51] Int. Cl.$^3$ .............................................. C07H 1/00
[52] U.S. Cl. .................................... 536/124; 536/120;
536/41; 568/394
[58] Field of Search ................. 536/120, 124; 568/594

[56] References Cited

U.S. PATENT DOCUMENTS 3,598,804  8/1971  Hindley et al. ...................... 536/124
3,607,862  9/1971  Jaffe et al. ............................ 536/124
3,622,560  11/1971 Hindley et al. ...................... 536/124

OTHER PUBLICATIONS

Adkins et al. *J. Amer. Chem. Soc.*, vol. 44, (1922) pp. 2749–2755.
Migrichian, *Organic Synthesis*, vol. 1, (1957) pp. 43–46.
Journal of American Chemical Society, 45, 734–751 (1923), Harold Hibbert and Harold S. Hill.
The Journal of the American Chemical Society 37 1748 (1915) ibid. 45, 734 (1923).

*Primary Examiner*—Johnnie R. Brown
*Assistant Examiner*—Elli Peselev
*Attorney, Agent, or Firm*—Wegner & Bretschneider

[57] ABSTRACT

A process is disclosed for production of a sugar ketal, which comprises reacting a sugar with a ketone in the presence of hydrogen iodide. The formation of unfavorable by-products can be reduced to a trace amount. The process offers the objective ketal in improved yields, and an industrially advantageous process.

12 Claims, No Drawings

PROCESS FOR PRODUCTION OF SUGAR KETALS

The present invention relates to a novel process for production of sugar ketals. More particularly, the present invention provides a process for producing sugar ketals in the presence of a catalyst. Production of sugar ketals is important for protection of hydroxyl groups of a sugar or for study of the structure of a sugar, and the sugar ketals are widely used as intermediates in various syntheses, for example, an intermediate for production of vitamin C, thus being very important from the industrial point of view.

The dehydration-condensation reaction of a sugar with a ketone is known as a ketal formation reaction, for which various methods have been proposed so far. The conventionally known methods involve the use of acid catalysts such as mineral acids exemplified by sulfuric acid, hydrogen chloride, hydrogen bromide, phosphoric acid and perchloric acid; organic acids exemplified by acetic acid, trifluoroacetic acid, methanesulfonic acid, p-toluenesulfonic acid and acidic ion exchange resins; or Lewis acids exemplified by anhydrous aluminum chloride, tin tetrachloride, boron trifluoride, anhydrous zinc chloride and ferric chloride. The ketal formation reaction is a dehydration-condensation reaction and, in almost all cases, the acid catalyst is used in large quantities so that the catalyst may serve as a dehydrating agent as well. When using a reduced amount of the acid catalyst it is necessary, furthermore, to use considerable quantities of dehydrating agents such as phosphorus pentoxide, calcium chloride, anhydrous sodium sulfate, anhydrous copper sulfate, pyrosulfates, metaphosphoric acid esters, alum and molecular sieves. That is to say, the conventional methods demand large quantities of acid catalysts and dehydrating agents. Therefore, the step of isolating the objective ketal from the reaction mixture is considerably troublesome. And a large amount of salts which are by-produced in the neutralization step and the used dehydrating agent are unfavorable industrial wastes. Thus, any one of the above conventional methods includes a good deal of problematic points as an industrial production process from the standpoints of post-treatment problems and saving of natural resources. In addition, these conventional methods entail a further disadvantage that side-reactions such as self-condensation of ketones are ready to take place, because the proposed catalysts are in every case strong acids. For example, U.S. Pat. Nos. 3,607,862 and 3,622,560 disclose the use of perchloric acid, ferric chloride and ferric bromide as a catalyst in the reaction of sugars and ketones. Though by use of these catalysts are much reduced production of unfavorable by-products such as a ketone dimer (e.g. acetone dimer) as compared with said conventional catalysts, these catalysts, however, still have a drawback to produce by-product to some extent.

The present inventors conducted an extensive investigation in order to eliminate such disadvantages as above, and have found that the reaction of a sugar with a ketone proceeds smoothly in the presence of hydrogen iodide, and the process is able to produce a sugar ketal in good yields and to decrease the formation of by-products.

Thus, the present invention is concerned with a process for producing a sugar ketal, which comprises reacting a sugar with ketone in the presence of hydrogen iodide.

The sugar usable in the present invention is not specifically limited, and is exemplified by a pentose such as arabinose, xylose, ribose, lyxose, ribulose and xylulose, a hexose such as glucose, galactose, talose, idose, gulose, mannose, altrose, fructose, sorbose, tagatose and psicose, a deoxy-sugar such as rhamnose, fucose, 2-deoxyribose, and 2-deoxyglucose, and a sugar alcohol such as ribitol, arabitol, mannitol, sorbitol, dulcitol and inositol. Among these sugars is valuable a pentose (e.g. arabinose and xylose) or a hexose (e.g. glucose, mannose, sorbose, galactose, fructose).

The ketone usable in the present invention is not specifically limited, and the preferred examples include an alkyl ketone such as acetone, methyl ethyl ketone, diethyl ketone, di-n-propyl ketone and di-i-propyl ketone, and a cyclic ketone such as cyclopentanone, cylohexanone and cycloheptanone. Among these ketones is valuable acetone or cyclohexanone. The amount of these ketones to be used varies depending upon the structure of the objective compounds. The ketone is normally used in about 1 to 10 times the theoretical molar quantity; for example, it is preferable to use 1 mole or more of a ketone per mole of a sugar in the case of the objective compound being a monoketal, to use 2 moles or more of a ketone per mole of a sugar in the case of the objective compound being a diketal, and to use 3 moles or more of a ketone per mole of a sugar in the case of the objective compound being a triketal. Furthermore, the ketones may be used both as a reactant and a solvent, and in such case, a large excess of them may be used, unless they give any adverse effect on the reaction.

Hydrogen iodide as used in the method of this invention may be hydrogen iodide as such or hydriodic acid obtainable by dissolving hydrogen iodide in water. Or, it may also be a compound or system that exists as hydrogen iodide in the reaction system or one that liberates hydrogen iodide in the reaction system.

Examples of the compound or system that exists as hydrogen iodide or liberates the same therein include, for example, (1) a metal iodide and an acid, (2) an iodination agent, and (3) an iodination agent and a reducing agent. Specific examples of said metal iodide are sodium iodide, potassium iodide, magnesium iodide, calcium iodide, ammonium iodide, lead iodide, etc., and those of said acid include phosphoric acid, nitric acid, sulfuric acid, hydrochloric acid, hydrobromic acid, trifluoroacetic acid, perchloric acid, etc. The said iodination agent is exemplified by iodine, iodine monochloride, iodine monobromide, iodine trichloride, phosphorus iodide, diphosphorus tetraiodide, N-iodosuccinimide, etc. and said reducing agent by hydrogen sulfide, hypophosphorous acid, sulfurous acid, hydrazine, etc.

The amount of hydrogen iodide used or that of hydrogen iodide made available in the reaction system may be at least about 0.01 weight percent, preferably in the range of a catalyst amount (about 0.03 wt. %) to about 20 wt. % and more desirably in the range of about 0.05 to 10 wt. %, all relative to the sugar.

The reaction solvent may be any solvent that will not interfere with the reaction and is exemplified by acetonitrile, propionitrile, nitromethane, nitroethane, nitrobenzene, dichloromethane, chloroform, carbon tetrachloride, 1,1-dichloroethane, 1,2-dichloroethane, ethyl bromide, pentane, cyclopentane, hexane, cyclohexane, heptane, benzene, toluene, xylene, etc. It is also possible to employ said ketone as the reaction solvent. Moreover, the reaction may also be conducted in a mixed solvent consisting of two or more of such solvents. Moreover, a small quantity of water may be added at the beginning of the reaction for the purpose of increasing the solubility of the sugar and catalyst in the solvent.

Since this reaction is an equilibrium reaction and the yield is generally improved when the water produced is removed, the reaction may be conducted with water being constantly removed from the reaction system by the known procedure. An example of such known procedure is distillative removal of water or the use of a drying agent. For distillative removal of water, azeotropic removal of water with a solvent is a generally accepted practice and in such procedure, the water is removed from the vapor condensate and the recovered solvent is returned to the reaction system. As an alternative, the azeotrope vapor may be expelled from the system and, instead, the same quantity of the dry solvent may be added to the reaction system. As an example of the technique using a drying agent, the azeotrope vapor or the condensate thereof is dried with a drying agent such as anhydrous calcium sulfate, molecular sieves, alumina, etc. and, then, returned to the reaction vessel.

The reaction temperature is generally in the range of about 0° C. to about 150° C., preferably about 20° C. to 100° C. The reaction may be conducted under reduced pressure to adjust the azeotropic point of the solvent or ketone and water.

While the reaction time depends on the kinds of sugars and ketones, the amount of catalyst and reaction conditions, it generally ranges from about 30 minutes to about 10 hours, preferably about 1 to 5 hours.

In order to isolate the sugar ketal thus produced from the reaction system, the reaction solvent may be distilled off as such, or after a small amount of alkalis (e.g., sodium hydrogencarbonate, potassium hydrogencarbonate, sodium carbonate, potassium carbonate, sodium hydroxide, potassium hydroxide, ammonia, pyridine, etc.) or aqueous solutions of said alkalis are added to adjust the pH of the reaction mixture to a weak alkalinity (a pH of about 7 to 9). The resultant residue, when subjected to the known separatory means such as extraction, distillation, column chromatography or recrystallization yields readily the objective sugar ketal.

The present invention provides an industrially advantageous process for producing sugar ketals.

The advantageous features of the method according to this invention are as follows. The acetalization reaction can be conducted at a sufficiently useful rate and selectively with the aid of a small amount of hydrogen iodide which has not been known to be a catalyst for this type of reaction and as a consequence, the aftertreatment of the reaction product is facilitated. In addition, the desired sugar ketal is obtained in high yield. Moreover, unlike the known methods, the method does not give industrial wastes. Since the amount of catalyst required is small or very small, there occur only very small amounts of by-products (e.g. ketone dimer). The reaction time is curtailed and the used catalyst can be easily recovered and reused.

The following examples illustrate the invention in more detail.

EXAMPLE 1

To a mixture of 100 ml of cyclohexanone and 100 ml of dichloromethane were added 10.0 g of D-arabinose and 175 mg of hydriodic acid (57%) and the mixture was refluxed with stirring in a water bath at 65° C. for 6 hours. During this reaction, the refluxing solvent was dried with 20 g of Molecular Sieves 3A (Wako Pure Chemical Industries, Ltd.) interposed between the reaction vessel and the cooling jacket. After completion of the reaction, a small amount of pyridine was added and the mixture was diluted with benzene, washed with aqueous sodium bicarbonate and water and dried over anhydrous magnesium sulfate. The solvent and cyclohexanone were distilled off under reduced pressure to give 20.67 g (100%) of di-O-cyclohexylidene-D-arabinose (purity $\geqq$ 98%). Melting point: 73.5°–75.5° C. (recrystallized from petroleum ether)

Elemental analysis: Calcd. for $C_{17}H_{26}O_5$: C, 65.78; H, 8.44. Found: C, 65.70; H, 8.50.

EXAMPLE 2

To 200 ml of acetone were added 10.0 g of D-xylose and 175 mg of hydriodic acid (57%) and the mixture was refluxed with stirring in a water bath at 60° C. for 5 hours. During this reaction, the refluxing solvent was dried with 20 g of Molecular Sieves 3A interposed between the reaction vessel and the cooling jacket. After completion of the reaction, a small amount of pyridine was added and the acetone was distilled off under reduced pressure. The residue was dissolved in benzene and the benzene solution was washed with aqueous sodium bicarbonate and water and dried over anhydrous magnesium sulfate. The benzene was distilled off under reduced pressure and the residue was further distilled under reduced pressure, whereby 12.8 g (83.6%) of 1,2:3,5-di-O-isopropylidene-α-D-xylofuranose was obtained as a fraction boiling at 94°–97° C./3 mmHg.

Elemental analysis: Calcd. for $C_{11}H_{18}O_5$: C, 57.58; H, 7.88. Found: C, 57.33; H, 7.60.

EXAMPLE 3

To a mixture of 150 ml of cyclohexanone and 120 ml of dichloromethane were added 10.0 g of D-xylose and 175 mg of hydriodic acid (57%) and the mixture was refluxed with stirring in a water bath at 65° C. for 8 hours. During this reaction, the refluxing solvent was dried with 20 g of Molecular Sieves 3A interposed between the reaction vessel and the cooling jacket. The reaction mixture was diluted with benzene, washed with aqueous sodium bicarbonate and water and dried over anhydrous magnesium sulfate. The solvent and cyclohexanone were distilled off under reduced pressure to give 19.8 g (96%) of 1,2:3,5-di-O-cyclohexylidene-α-D-xylofuranose. After recrystallization from petroleum ether, it melted at 104.5°–105.5° C.

Elemental analysis: Calcd. for $C_{17}H_{26}O_5$: C, 65.78; H, 8.44. Found: C, 66.14; H, 8.47.

EXAMPLE 4

To 200 ml of acetone were added 10.0 g of D-ribose and 175 mg of hydriodic acid (57%) and the mixture was refluxed with stirring in a water bath at 60° C. for 6 hours. During this reaction, the refluxing solvent was dried with 20 g of Molecular Sieves 3A interposed between the reaction vessel and the cooling jacket. After completion of the reaction, a small amount of aqueous sodium bicarbonate was added. The acetone was then distilled off under reduced pressure, and the residue was dissolved in benzene, washed with aqueous sodium bicarbonate and water and dried over anhydrous sodium sulfate. The benzene was distilled off under reduced pressure and the residue was further distilled under reduced pressure, whereby 3.84 g (30%) of 2,3-O-isopropylidene-D-ribofuranose was obtained as a fraction boiling at 108°–111° C./0.04 mmHg.

Elemental analysis: Calcd. for $C_8H_{14}O_5$: C, 50.52; H, 7.42. Found: C, 50.49; H, 7.40.

EXAMPLE 5

To 200 ml of acetone were added 10.0 g of D-glucose and 100 mg of hydrogen iodide and the mixture was refluxed with stirring in a water bath at 60° C. for 8 hours. During this reaction, the refluxing solvent was dried with 20 g of Molecular Sieves 3A interposed between the reaction vessel and the cooling jacket. After completion of the reaction, a small amount of pyridine was added. The acetone was then distilled off under reduced pressure and the residue was dissolved in benzene, washed with aqueous sodium bicarbonate and water and dried over anhydrous magnesium sulfate. The benzene was distilled off under reduced pressure to give 11.5 g (80.0%) of 1,2:5,6-di-O-isopropylidene-α-D-glucofuranose. After recrystallization from chloroform-hexane (1:2), it melted at 107°–109° C.

Elemental analysis: Calcd. for $C_{12}H_{20}O_6$: C, 55.37; H, 7.75. Found: C, 55.74; H, 7.81.

EXAMPLE 6

To a mixture of 150 ml of cyclohexanone and 120 ml of dichloromethane were added 10.0 g of D-glucose and 175 mg of hydriodic acid (57%) and the mixture was refluxed with stirring in a water bath at 65° C. for 8 hours. During this reaction, the refluxing solvent was dried with 20 g of Molecular Sieves 3A interposed between the reaction vessel and the cooling jacket. The reaction mixture was diluted with chloroform, washed with aqueous sodium bicarbonate and water and dried over anhydrous magnesium sulfate. The solvent and cyclohexanone were distilled off under reduced pressure and the residue was recrystallized from ligroin to give 11.2 g (77.8%) of 1,2:5,6-di-O-cyclohexylidene-α-D-glucofuranose, melting at 133°–136° C.

Elemental analysis: Calcd. for $C_{18}H_{28}O_6$: C, 63.51; H, 8.29. Found: C, 63.27; H, 8.34.

EXAMPLE 7

To 200 ml of acetone were added 10.0 g of D-galactose and 175 mg of hydriodic acid (57%) and the mixture was refluxed with stirring in a water bath at 60° C. for 8 hours. During this reaction, the refluxing solvent was dried with 20 g of Molecular Sieves 3A interposed between the reaction vessel and the cooling jacket. After completion of the reaction, a small amount of pyridine was added. The acetone was then distilled off under reduced pressure and the residue was dissolved in benzene, washed with aqueous sodium bicarbonate and water and dried over anhydrous magnesium sulfate. The benzene was distilled off and the residue was further distilled under reduced pressure, whereby 8.5 g (59%) of 1,2:3,4-di-O-isopropylidene-α-D-galactopyranose was obtained as a fraction boiling at 129°–133° C./0.2 mmHg.

Elemental analysis: Calcd. for $C_{12}H_{20}O_6$: C, 55.37; H, 7.75. Found: C, 55.01; H, 7.80.

EXAMPLE 8

To 200 ml of acetone were added 10.0 g of D-mannose and 100 mg of hydrogen iodide and the mixture was refluxed with stirring in a water bath at 60° C.for 5 hours. During this reaction, the refluxing solvent was dried with 20 g of Molecular Sieves 3A interposed between the reaction vessel and the cooling jacket. After completion of the reaction, a small amount of pyridine was added. The acetone was then distilled off under reduced pressure and the residue was dissolved in benzene, washed with aqueous sodium bicarbonate and water and dried over anhydrous magnesium sulfate. The benzene was distilled off under reduced pressure to give 11.5 g (80%) of 2,3:5,6-di-O-isopropylidene-α-D-mannofuranose. After recrystallization from petroleum ether, it melted at 122°–123° C.

Elemental analysis: Calcd. for $C_{12}H_{20}O_6$: C, 55.37; H, 7.75. Found: C, 55.41; H, 7.78.

EXAMPLE 9

To a mixture of 150 ml of cyclohexanone and 120 ml of dichloromethane were added 10.0 g of D-mannose and 175 mg of hydriodic acid (57%) and the mixture was refluxed with stirring in a water bath at 65° C. for 8 hours. During this reaction, the refluxing solvent was dried with 20 g of Molecular Sieves 3A interposed between the reaction vessel and the cooling jacket. The reaction mixture was diluted with benzene, washed with aqueous sodium bicarbonate and water and dried over anhydrous magnesium sulfate. The solvent and cyclohexanone were distilled off under reduced pressure to give 11.9 g (82.6%) of 2,3:5,6-di-O-cyclohexylidene-α-D-mannofuranose. After recrystallization from cyclohexane, it melted at 122°–124° C.

Elemental analysis: Calcd. for $C_{18}H_{28}O_6$: C, 63.51; H, 8.29. Found: C, 63.17; H, 8.32.

EXAMPLE 10

To 200 ml of acetone were added 10.0 g of D-fructose and 175 mg of hydriodic acid (57%) and the mixture was refluxed with stirring in a water bath at 60° C. for 6 hours. During this reaction, the refluxing solvent was dried with 20 g of Molecular Sieves 3A interposed between the reaction vessel and the cooling jacket. After completion of the reaction, a small amount of pyridine was added. The acetone was then distilled off under reduced pressure, and the residue was dissolved in benzene. The benzene solution was washed with aqueous sodium bicarbonate and water and dried over anhydrous magnesium sulfate. The benzene was distilled off under reduced pressure to give 10.7 g (74.3%) of 2,3:4,5-di-O-isopropylidene-α-D-fructopyranose. After recrystallization from n-hexane, it melted at 96°–98° C.

Elemental analysis: Calcd. for $C_{12}H_{20}O_6$: C, 55,37; H, 7.75. Found: C, 55.61; H, 7.77.

EXAMPLE 11

To 200 ml of acetone were added 10.0 g of L-sorbose and 223 mg of hydriodic acid (57%) and the mixture was refluxed with stirring in a water bath at 60° C. for 6 hours. During this reaction, the refluxing solvent was dried with 20 g of Molecular Sieves 3A interposed between the reaction vessel and the cooling jacket. After completion of the reaction, a small amount of pyridine was added. The acetone was then distilled off under reduced pressure and the residue was dissolved in benzene. The benzene solution was washed with aqueous sodium bicarbonate and water and dried over anhydrous magnesium sulfate. The benzene was distilled off under reduced pressure to give 12.13 g (84.0%) of 2,3:4,6-di-O-isopropylidene-L-sorbofuranose (purity ≧98%). Melting point: 77°–78° C. (recrystallized from petroleum ether).

Elemental analysis: Calcd. for $C_{12}H_{20}O_6$: C, 55.37; H, 7.75. Found: C, 55.40; H, 7.80.

EXAMPLE 12

To 200 ml of acetone were added 10.0 g of L-sorbose and 127 mg of iodine and the mixture was refluxed with stirring in a water bath at 60° C. for 6 hours. During this reaction, the refluxing solvent was dried with 20 g of Molecular Sieves 3A interposed between the reaction vessel and the cooling jacket. The reaction mixture was then subjected to an after-treatment similar to that described in Example 11 to give 11.15 g (77.2%) of 2,3:4,6-di-O-isopropylidene-L-sorbofuranose (purity ≧98.5%).

EXAMPLE 13

To 200 ml of acetone were added 10.0 g of L-sorbose and 81.5 mg of iodine monochloride and the mixture was refluxed with stirring in a water bath at 60° C. for 6 hours. During this reaction, the refluxing solvent was dried with 20 g of Molecular Sieves 3A interposed between the reaction vessel and the cooling jacket. The reaction mixture was then subjected to an after-treatment similar to that described in Example 11 to give 10.9 g (75.8%) of 2,3:4,6-di-O-isopropylidene-L-sorbofuranose (purity ≧97%).

EXAMPLE 14

To 200 ml of acetone were added 10.0 g of L-sorbose and 234 mg of iodine trichloride and the mixture was refluxed with stirring in a water bath at 60° C. for 4 hours. During this reaction, the refluxing solvent was dried with 20 g of Molecular Sieves 3A interposed between the reaction vessel and the cooling jacket. The reaction mixture was then subjected to an after-treatment similar to that described in Example 11 to give 9.85 g (68.2%) of 2,3:4,6-di-O-isopropylidene-L-sorbofuranose (purity ≧98%).

EXAMPLE 15

To 200 ml of acetone were added 10.0 g of L-sorbose and 225 mg of N-iodosuccinimide and the mixture was refluxed with stirring in a water bath at 60° C. for 6 hours. During this reaction, the refluxing solvent was dried with 20 g of Molecular Sieves 3A interposed between the reaction vessel and the cooling jacket. The reaction mixture was then subjected to an after-treatment similar to that described in Example 11 to give 8.43 g (58.4%) of 2,3:4,6-di-O-isopropylidene-L-sorbofuranose (purity ≧97%).

EXAMPLE 16

To 200 ml of acetone were added 10.0 g of L-sorbose, 166 mg of potassium iodide and 152 mg of conc. sulfuric acid and the mixture was refluxed with stirring in a water bath at 60° C. for 4 hours. During this reaction, the refluxing solvent was dried with 20 g of Molecular Sieves 3A interposed between the reaction vessel and the cooling jacket. The reaction mixture was then subjected to an after-treatment similar to that described in Example 11 to give 6.79 g (47.0%) of 2,3:4,6-di-O-isopropylidene-L-sorbofuranose (purity ≧96%).

EXAMPLE 17

To a mixture of 150 ml of cyclohexanone and 120 ml of dichloromethane were added 10.0 g of L-sorbose and 175 mg of hydriodic acid (57%) and the mixture was refluxed with stirring in a water bath at 65° C. for 8 hours. During this reaction, the refluxing solvent was dried with 20 g of Molecular Sieves 3A interposed between the reaction vessel and the cooling jacket. The reaction mixture was diluted with benzene, washed with aqueous sodium bicarbonate and water and dried over anhydrous magnesium sulfate. The solvent and cyclohexanone were distilled off under reduced pressure to give 8.4 g (44.4%) of 2,3:4,6-di-O-cyclohexylidene-L-sorbofuranose. After recrystallization from petroleum ether, it melted at 118°–119° C.

Elemental analysis: Calcd. for $C_{18}H_{28}O_6$: C, 63.51; H, 8.29. Found: C, 63.72; H, 8.24.

EXAMPLE 18

To a mixture of 150 ml of cyclohexanone and 120 ml of dichloromethane were added 10.0 g of L-sorbose and 254 mg of iodine and the mixture was refluxed with stirring in a water bath at 65° C. for 8 hours. During this reaction, the refluxing solvent was dried with 20 g of Molecular Sieves 3A interposed between the reaction vessel and the cooling jacket. The reaction mixture was diluted with benzene, washed with aqueous sodium bicarbonate and water and dried over anhydrous magnesium sulfate. The solvent and cyclohexanone were distilled off under reduced pressure to give 12.3 g (65%) of 2,3:4,6-di-O-cyclohexylidene-L-sorbofuranose. After recrystallization from petroleum ether, it melted at 118°–119° C.

Elemental analysis: Calcd. for $C_{18}H_{28}O_6$: C, 63.51; H, 8.29. Found: C, 63.76; H, 8.38.

EXAMPLE 19

To 200 ml of acetone were added 10.0 g of D-mannitol and 175 mg of hydriodic acid (57%) and the mixture was refluxed with stirring in a water bath at 60° C. for 5 hours. During this reaction, the refluxing solvent was dried with 20 g of Molecular Sieves 3A interposed between the reaction vessel and the cooling jacket. After completion of the reaction, a small amount of pyridine was added. The acetone was then distilled off under reduced pressure and the residue was dissolved in chloroform. The solution was washed with aqueous sodium bicarbonate and water and dried over anhydrous magnesium sulfate. The chloroform was distilled off under reduced pressure to give 15.0 g (90%) of 1,2:3,4:5,6-tri-O-isopropylidene-D-mannitol. After recrystallization from 70% ethanol, it melted at 68.5°–70.5° C.

Elemental analysis: Calcd. for $C_{15}H_{26}O_6$: C, 59.58; H, 8.67. Found: C, 59.77; H, 8.58.

EXAMPLE 20

To 200 ml of acetone were added 10.0 g of L-sorbose and 57 mg of diphosphorus tetraiodide and the mixture was refluxed with stirring in a water bath at 60° C. for 4 hours. During this reaction, the refluxing solvent was dried with 20 g of Molecular Sieves 3A interposed between the reaction vessel and the cooling jacket. The reaction mixture was then subjected to an after-treatment similar to that described in Example 11 to give 8.60 g (59.5%) of 2,3:4,6-di-O-isopropylidene-L-sorbofuranose (purity ≧90%).

EXAMPLE 21

To 200 ml of acetone were added 10.0 g of L-sorbose, 90 mg of hydriodic acid (57%) and 50.8 mg of iodine and the mixture was refluxed with stirring in a water bath at 60° C. for 8 hours. During this reaction, the refluxing solvent was dried with 20 g of Molecular Sieves 3A interposed between the reaction vessel and the cooling jacket. The reaction mixture was then subjected to an after-treatment similar to that described in Example 11 to give 12.07 g (83.6%) of 2,3:4,6-di-O-isopropylidene-L-sorbofuranose (purity ≧98%).

EXAMPLE 22

To 200 ml of acetone were added 10.0 g of L-sorbose, 127 mg of iodine and 110 mg of aqueous hypophosphorous acid solution (about 30%) and the mixture was refluxed with stirring in a water bath at 60° C. for 6 hours. During this reaction, the refluxing solvent was dried with 20 g of Molecular Sieves 3A interposed between the reaction vessel and the cooling jacket. The reaction mixture was then subjected to an after-treatment similar to that described in Example 11 to give 11.56 g (80.0%) of 2,3:4,6-di-O-isopropylidene-L-sorbofuranose (purity ≧98%).

What we claimed is:

1. A process for producing a sugar ketal which comprises reacting a sugar of the class consisting of the pentoses, hexoses, rhamnose, fucose, deoxyribose, deoxyglucose, ribitol, arabitol, mannitol, sorbitol and inositol with a ketone of the group consisting of di-($C^{1-3}$-alkyl)ketones and $C^{5-7}$-cycloalkanones in the presence of hydrogen iodide.

2. A process according to claim 1, wherein the sugar is a pentose or a hexose.

3. A process according to claim 2, wherein the hexose is sorbose or glucose.

4. A process according to claim 1, wherein the ketone is acetone.

5. A process according to claim 1, wherein the hydrogen iodide is reacted in the form of hydriodic acid obtained by dissolving hydrogen iodide in water.

6. A process according to claim 1, wherein the hydrogen iodide is reacted in the form of a compound or system that exists as hydrogen iodide in the reaction system or one that liberates hydrogen iodide in the reaction system.

7. A process according to claim 6, wherein the compound is an iodination agent.

8. A process according to claim 7, wherein the iodination agent is iodine, iodine monochloride, iodine trichloride, N-iodosuccinimide, phosphorus iodide or diphosphorus tetraiodide.

9. A process according to claim 6, wherein the system is a metal iodide and an acid.

10. A process according to claim 9, wherein the metal iodide is sodium iodide, and the acid is sulfuric acid.

11. A process according to claim 9, wherein the system is an iodination agent and a reducing agent.

12. A process according to claim 11, wherein the iodination agent is iodine, and the reducing agent is hypophosphorous acid.

* * * * *